(12) United States Patent
Attolino et al.

(10) Patent No.: US 9,932,321 B2
(45) Date of Patent: Apr. 3, 2018

(54) PROCESS FOR THE PREPARATION OF PIPERIDINE COMPOUNDS

(71) Applicant: DIPHARMA FRANCIS s.r.l, Baranzate (IT)

(72) Inventors: Emanuele Attolino, Baranzate (IT); Davide Rossi, Baranzate (IT); Gabriele Razzetti, Baranzate (IT)

(73) Assignee: Dipharma Francis S.R.L., Baranzate (IT)

(*) Notice: Subject to any disclaimer, the term of this patent is extended or adjusted under 35 U.S.C. 154(b) by 0 days.

(21) Appl. No.: 15/194,773

(22) Filed: Jun. 28, 2016

(65) Prior Publication Data

US 2016/0376253 A1 Dec. 29, 2016

(30) Foreign Application Priority Data

Jun. 29, 2015 (IT) .................. 102015000028717

(51) Int. Cl.
*C07D 401/06* (2006.01)
(52) U.S. Cl.
CPC ................. *C07D 401/06* (2013.01)

(58) Field of Classification Search
None
See application file for complete search history.

(56) References Cited

U.S. PATENT DOCUMENTS

| 5,620,994 A | 4/1997 | Naito et al. |
| 8,871,942 B2 | 10/2014 | Mimura et al. |
| 2013/0150586 A1 | 6/2013 | Mimura et al. |

OTHER PUBLICATIONS

Chakraborti et al., "Lithium Bromide, an Inexpensive and Efficient Catalyst for Opening of Epoxide Rings by Amines at Room Temperature under Solvent-Free Condition", Eur. J. Org. Chem., Aug. 2004, pp. 3597-3600.
Ogura et al., "Synthesis and Antifungal Activities of (2R,3R)-2-Aryl-1-azolyl-3-(substituted amino)-2-butanol Derivatives as Topical Antifungal Agents", Chem. Pharm. Bull, 47(10), pp. 1417-1425 (1999).
Italian Search Report dated Feb. 16, 2016, 3 pages.

*Primary Examiner* — Zinna Northington Davis
(74) *Attorney, Agent, or Firm* — Rothwell, Figg, Ernst & Manbeck, P.C.

(57) ABSTRACT

The present invention relates to a process for the preparation of efinaconazole.

13 Claims, No Drawings

PROCESS FOR THE PREPARATION OF PIPERIDINE COMPOUNDS

FIELD OF INVENTION

The present invention relates to a process for the preparation of efinaconazole.

PRIOR ART (2R,3R)-2-(2,4-difluorophenyl)-3-(4-methylenepiperidinyl)-1-(1H-1,2,4-triazolyl)butan-2-ol of formula (I), also known as efinaconazole, is an active pharmaceutical ingredient belonging to the class of triazole antifungals, which is used in the topical treatment of distal and lateral subungual onychomycosis (DLSO), a chronic infection of the ungual apparatus mainly caused by dermatophytes and yeasts and characterised by discolouring, thickening and deformity of the nail.

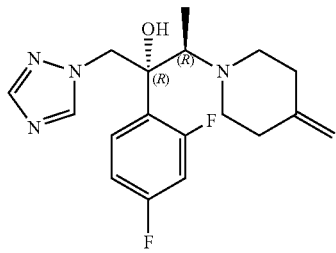

(I)

The 10% topical solution of efinaconazole is marketed under the name of Jublia®. Efinaconazole is known from EP0698606, which describes its preparation by means of a process comprising opening of the optically pure epoxide of formula (II) with the 4-methylenepiperidine of formula (IIIa), according to Scheme 1 below.

Scheme 1

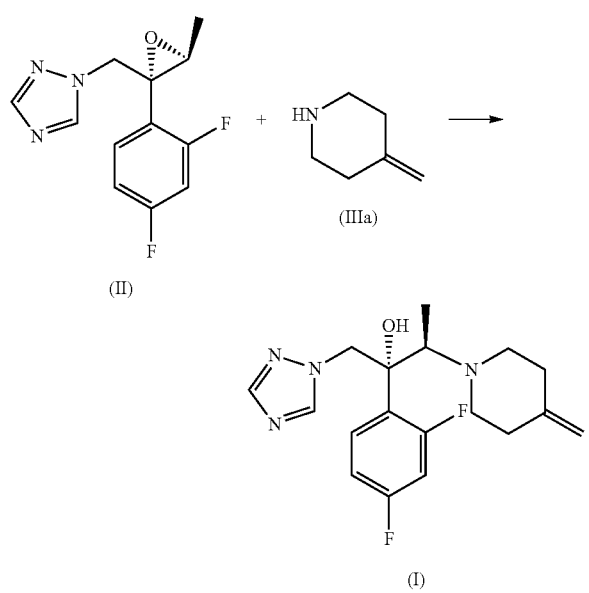

The reaction is conducted in water or a mixture of water/organic solvent, which can be an ether, an alcohol or an amide, at reflux, in the presence of a large excess of amine of formula (IIIa), namely 5 to 20 times the moles of epoxytriazole of formula (II). Under said conditions, the reaction leads to the formation of efinaconazole together with various by-products. Purification of the crude reaction product by chromatography or crystallisation therefore allows the isolation of efinaconazole with a yield not exceeding 54%.

U.S. Pat. No. 8,871,942 describes a synthesis of efinaconazole, which involves opening the epoxytriazole of formula (II) in the presence of 1.5 equivalents of a 4-methylenepiperidine salt of formula (III) (preferably hydrobromide) and 1.5 equivalents of a lithium, strontium or calcium hydroxide in an appropriate solvent, as shown in Scheme 2 below.

Scheme 2

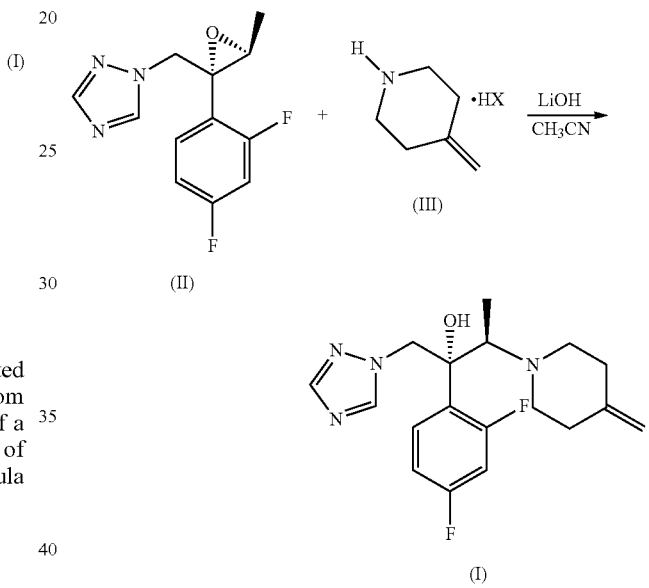

The reaction with lithium hydroxide in acetonitrile at reflux according to Example 1 of U.S. Pat. No. 8,871,942 is described as proceeding in 14 hours and providing efinaconazole with a yield of 87.3% and an HPLC purity of 95.3%.

The authors of the present invention attempted to reproduce the above-reported procedure exactly. By monitoring the progress of the reaction by HPLC analysis, it was found that the reaction was complete after no less than 40 hours, when the quantity of residual epoxytriazole of formula (II) was lower than 2%. Throughout its duration the reaction presented as a biphasic system due to the presence of undissolved solids. The product was therefore obtained with a yield almost identical to that declared by the inventors in U.S. Pat. No. 8,871,942, and with a purity of around 95%. However, although this latter process represents an improvement on the synthesis of efinaconazole, it still cannot be considered optimal. The lithium hydroxide employed to release the salt of formula (III) is used in excess relative to the epoxytriazole of formula (II), namely at least 1.5 equivalents, and generates many salts insoluble in the reaction medium, which make the system non-homogenous and produce a large amount of aqueous wastewater. The reaction on the whole is still rather slow, and efinaconazole is isolated with insufficient purity to comply with the Pharmacopoeia specifications; therefore, further crystallisations are necessary.

There is consequently a need for an efinaconazole synthesis method which involves shorter reaction times and prevents the formation of biphasic or non-homogenous systems, thus also preventing the formation of large amounts of wastewater. A novel method of this kind should, in particular, involve the use of efficient, low-cost, operationally simple reaction conditions in order to obtain efinaconazole or a salt thereof advantageously, in particular on an industrial scale, with high chemical purity and stereochemistry.

SUMMARY OF THE INVENTION

The invention provides a process for the preparation of efinaconazole of formula (I) or a salt thereof,

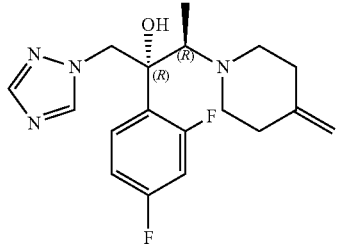
(I)

comprising the reaction between a compound of formula (II)

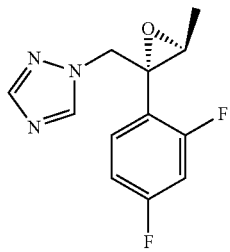
(II)

and a salt of formula (III)

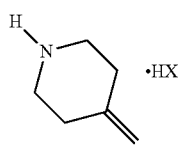
(III)

wherein HX is a strong organic or mineral acid, in the presence of a strong organic base and a lithium salt in an organic solvent and, if desired, the conversion of efinaconazole of formula (I) to a salt thereof or vice versa.

DETAILED DESCRIPTION OF THE INVENTION

The subject of the present invention is a process for the preparation of efinaconazole of formula (I), or a salt thereof,

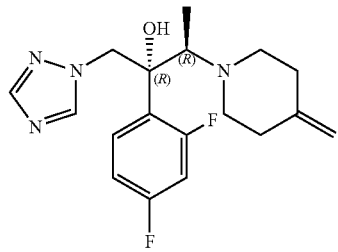
(I)

comprising the reaction between a compound of formula (II)

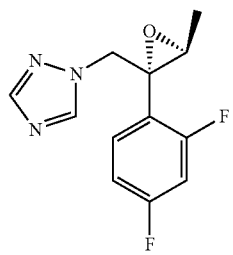
(II)

and a salt of formula (III)

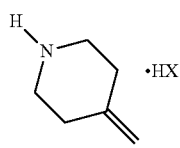
(III)

wherein HX is a strong organic or mineral acid, in the presence of a strong organic base and a lithium salt in an organic solvent and, if desired, the conversion of efinaconazole of formula (I) to a salt thereof or the conversion of a salt of efinaconazole into the free product.

An efinaconazole salt is typically a pharmaceutically acceptable salt thereof, such as the p-toluenesulfonate salt.

A strong organic or mineral acid is typically an acid having a pKa, measured in an aqueous medium, of less than 1.

A strong organic acid HX can be selected from the group comprising a $C_2$-$C_4$ carboxylic acid substituted with three halogen atoms, for example with three atoms of chlorine or fluorine, such as trichloroacetic acid or trifluoroacetic acid; and a sulfonic acid optionally substituted with one or more halogen atoms, such as methanesulfonic acid, trifluoromethanesulfonic acid, p-toluenesulfonic acid or camphorsulfonic acid.

A strong mineral acid HX can be selected from the group comprising a hydrohalic acid, such as hydrochloric acid, hydrobromic acid or hydroiodic acid; sulfuric acid; and nitric acid.

The strong acid HX is preferably hydrobromic acid.

The strong organic base is typically a base having a pKa, measured in an aqueous medium, greater than 11.

The strong organic base can be selected from the group comprising an alkali metal alkoxide, such as sodium tert-butoxide or potassium tert-butoxide; an alkali metal hydride, such as sodium hydride or potassium hydride; and a tertiary amine such as diazabicycloundecene (DBU); 2,2,6,6-tetramethyl piperidine or 1,1,3,3-tetramethylguanidine.

The strong organic base is preferably 1,1,3,3-tetramethylguanidine.

The lithium salt is a salt of formula $$Li_nY$$

wherein n is an integer, which may be 1 or 2, and Y is a weakly coordinating or non-coordinating anion.

A weakly coordinating or non-coordinating anion can be typically selected from the group comprising azide, sulfate, nitrate, $C_1$-$C_6$ alkylsulfonate, $C_1$-$C_6$ alkylsulfinate, $C_1$-$C_6$ alcoholate, phenolate, $C_1$-$C_6$ alkylcarboxylate, perchlorate, tetrafluoroborate and hexafluorophosphate.

It has been found that the lithium salt is particularly efficient, when Y is a non-coordinating anion such as perchlorate or nitrate. Therefore, according to a particularly preferred aspect of the invention, Y is a non-coordinating anion such as perchlorate or nitrate.

According to a particularly preferred aspect of the invention, the lithium salt is lithium nitrate.

The lithium salt is typically used in a molar amount ranging about from 0.5 to 2.00, preferably about from 1 to 1.5, based on the compound of formula (II).

The reaction can be conducted in a solvent selected from the group comprising a polar aprotic solvent such as dimethylformamide, dimethylsulfoxide or acetonitrile; an ether solvent such as tetrahydrofuran or dioxane; a ketone such as methyl ethyl ketone, methyl isobutyl ketone or acetone; an apolar aprotic solvent such as hexane, heptane, toluene or xylene; a polar protic solvent such as a straight or branched $C_1$-$C_5$ alkanol, preferably ethanol or isopropanol; or a mixture of two or more, typically two or three, of said solvents.

According to a preferred aspect of the invention, the reaction can be conducted in the presence of acetonitrile.

Said reaction can be conducted at a temperature ranging between about 0° C. and the reflux temperature of the solvent, preferably at the reflux temperature.

Efinaconazole of formula (I) can be converted into a salt thereof by known methods, for example by treating efinaconazole with an acid, such as p-toluenesulfonic acid.

An efinaconazole salt of formula (I) can be converted to efinaconazole of formula (I) as free base by methods known to the prior art, for example by treating the efinaconazole salt of formula (I) with an aqueous solution of a base, such as sodium hydroxide.

An efinaconazole salt, such as efinaconazole p-toluenesulfonate, is preferably converted into efinaconazole free base by dissolving efinaconazole p-toluenesulfonate in a methanol/water mixture and subsequently adding a 30% solution of sodium hydroxide.

Efinaconazole or a salt thereof is obtained with high yields and purity by the process according to the invention.

It has been found that in the synthesis of an efinaconazole by the processes known to the prior art, two impurities, of formulas (A) and (B), are often generated.

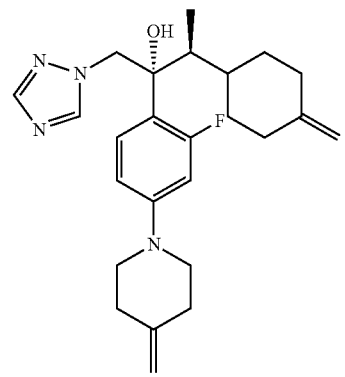

(A)

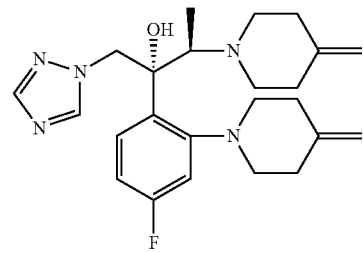

(B)

Said impurities of formulas (A) and (B) are generated by attachment of the amine of formula (IIIa),

(IIIa)

which forms during the reaction from the release of the salt of formula (III) on the para and ortho positions respectively of the fluorinated aromatic ring of efinaconazole or of a compound of formula (II).

Surprisingly, efinaconazole or a salt thereof, in particular prepared by the process according to the invention, presents at least one compound of formula (A) and/or formula (B) in quantities below 0.1%, preferably equal to or lower than 0.05% as HPLC area % (A %) at 210 nm.

A further subject of the present invention is therefore efinaconazole or a salt thereof which contains a compound of formula (A) and/or formula (B) in quantities below 0.1%, preferably equal to or lower than 0.05% as HPLC area % (A %) at 210 nm.

A further subject of the present invention is a composition comprising efinaconazole or a salt thereof and a compound of formula (A) in quantities below 0.1%, preferably equal to or lower than 0.05% as HPLC area % (A %) at 210 nm.

A further subject of the present invention is a composition comprising efinaconazole or a salt thereof and a compound of formula (B) in quantities below 0.1%, preferably equal to or lower than 0.05% as HPLC area % (A %) at 210 nm.

The following examples further illustrate the invention.

EXAMPLE 1: Synthesis of Efinaconazole p-Toluenesulfonate 40 ml of acetonitrile, 6.47 g of 1,1,3,3-tetramethylguanidine (56.16 mmol), 10.0 (g) of 4-methylenepiperidine hydrobromide (56.16 mmol), 2.58 g of lithium nitrate (37.44 mmol) and 9.41 g of compound of formula (II) (37.44 mmol) are introduced into a 250 ml multi-necked flask under nitrogen atmosphere. The reaction mixture is heated to reflux, and the reaction ends after 30 hours; the mixture is then cooled to 20-25° C. and diluted with 20 ml of water, 20 ml of acetonitrile and 5 ml of saturated NaCl solution. The phases are separated, the aqueous phase is extracted with 20 ml of ethyl acetate, and the combined organic phases are concentrated, to obtain a residue, which is dissolved in 75 ml of methanol, heated to 30° C. and treated with water. The mixture is cooled to 20° C., maintained under those conditions for one hour and filtered off; the solid is then suspended in 45 ml of isopropanol. The mixture is heated to 70° C. and treated with 4.95 g of p-toluenesulfonic acid monohydrate. The mixture is maintained at reflux temperature for 3 hours and then cooled to 20° C. and filtered off. The resulting solid is washed with isopropanol and dried at 50° C. under vacuum, to provide 11.99 g of efinaconazole p-toluenesulfonate salt with a yield of 67% and an HPLC purity greater than 99%, calculated as HPLC area % (A %) at 210 nm.

EXAMPLE 2: Release of Efinaconazole p-Toluenesulfonate Salt 10.0 g of p-toluenesulfonic acid efinaconazole salt (19.21 mmol), obtained according to Example 1, 20 ml of a 4:1 methanol/water mixture and 0.2 g of charcoal are loaded into a 50 ml multi-necked flask under nitrogen atmosphere and heated at 50-55° C. for 30 minutes. The mixture is then filtered through a perlite panel, the solution is transferred to a 100 ml multi-necked flask fitted with a mechanical stirrer, and 2.82 g of 30% NaOH (21.13 mmol) is added dropwise. The mixture is then cooled to 30-35° C., 5 ml of water is added dropwise, and it is triggered with efinaconazole (I). The mixture is left under stirring for about 30 minutes, and a further 30 ml of water is then added dropwise; the mixture is then cooled to 20-25° C., maintained under those conditions for one hour, and the formed solid is filtered off. After drying at 50° C. under vacuum, 6.50 g of efinaconazole (I), with an HPLC purity greater than 99.5% calculated as HPLC area % (A %) at 210 nm, and a yield of 97%, is obtained.

EXAMPLE 3: Synthesis of Efinaconazole p-Toluenesulfonate Salt 4-methylenepiperidine p-toluenesulfonate (96.5 g, 358 mmol) in acetonitrile (97 ml) is suspended in a 500 ml flask, fitted with mechanical blade stirrer, thermometer and bubble condenser, in an inert atmosphere, and 1,1,3,3 tetramethylguanidine (44.0 g, 382 mmol) is added by slow dripping. The mixture is cooled to 0° C. and the solid is discarded by filtration, washing it twice with 80 ml of acetonitrile. Lithium nitrate (24.7 g, 358 mmol) and (2R,3S)-2-(2,4-difluorophenyl)-3-methyl-2-[(1H-1,2,4-triazolyl)methyl] oxirane (60.0 g, 239 mmol) are added to the solution. The mixture is heated to reflux for 38 hours, and water (120 ml) and toluene (120 ml) are added after cooling to 20° C. The aqueous phase is counter-extracted with toluene (45 ml), and the combined organic phases are concentrated at low pressure. The residue is taken up with methanol (400 ml), and the solid efinaconazole is precipitated by adding water (400 ml). After cooling to 10° C. the product is filtered off and dried at 55° C., providing efinaconazole (68.3 g, 196 mmol) as a yellow/orange solid with a yield of 82%. 150 g (789 mmol) of p-toluenesulfonic acid (PTSA) monohydrate are added to 250 g (718 mmol) of efinaconazole suspended under nitrogen atmosphere in 1250 ml of isopropanol in a three necks flask and the mixture is heated at 70° C. for about 3 h. After cooling down to room temperature the product is filtered off, rinsed with 300 ml of isopropanol and dried providing 335 g (yield: 90%) of efinaconazole as its p-toluensulfonate salt, with an HPLC purity greater than 99%, calculated as HPLC area % (A %) at 210 nm.

The invention claimed is:

1. A process for the preparation of efinaconazole of formula (I), or a salt thereof,

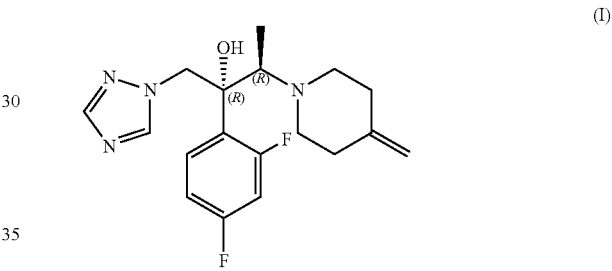

(I)

comprising the reaction between a compound of formula (II)

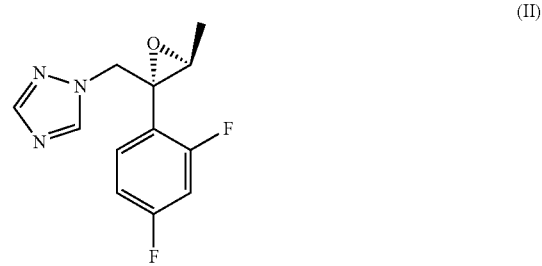 [SMILES: C[C@@H]1O[C@@]1(Cn1cncn1)c1ccc(F)cc1F]

(II)

and a salt of formula (III)

(III)

wherein HX is a strong organic or mineral acid,
in the presence of a strong organic base and of a lithium salt in a solvent and, if desired, the conversion of efinaconazole of formula (I) into a salt thereof or the conversion of a salt of efinaconazole into the free compound,
wherein the lithium salt is lithium nitrate.

2. The process according to claim 1, wherein the strong organic base is a base having a pKa, measured in aqueous environment, greater than 11.

3. The process according to claim 1, wherein the strong organic base is selected from the group consisting of an alkali metal alkoxide, an alkali metal hydride, and a tertiary amine.

4. The process according to claim 1, wherein the strong organic base is selected from the group consisting of diazabicycloundecene (DBU), 2,2,6,6-tetramethyl piperidine and 1,1,3,3-tetramethylguanidine.

5. The process according to claim 1, wherein the strong organic base is 1,1,3,3-tetramethylguanidine.

6. The process according to claim 1, wherein the strong organic acid is selected from the group consisting of a $C_2$-$C_4$ carboxylic acid substituted by three halogen atoms, and a sulfonic acid optionally substituted by one or more halogen atoms.

7. The process according to claim 1, wherein the strong mineral acid is selected from the group consisting of a hydrohalic acid and nitric acid.

8. The process according to claim 1, wherein the strong mineral acid is hydrobromic acid.

9. The process according to claim 1, wherein the strong acid is an acid having a pKa, measured in aqueous environment, lower than 1.

10. The process according to claim 1, wherein the solvent is selected from the group consisting of an aprotic polar solvent; an ether; a ketone; an aprotic apolar solvent; a protic polar solvent and water, and a mixture of two or three of said solvents.

11. The process according to claim 1, wherein the solvent is acetonitrile.

12. A composition comprising efinaconazole or an efinaconazole salt, in combination with a compound of formula (A)

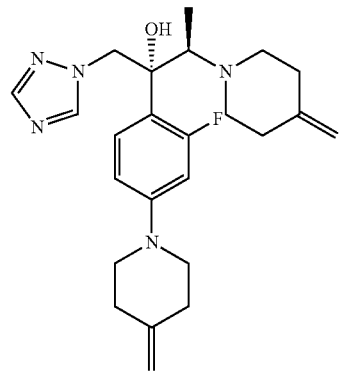

in quantities below 0.1% calculated as HPLC area % (A %) at 210 nm.

13. A composition comprising efinaconazole or an efinaconazole salt in combination with a compound of formula (B)

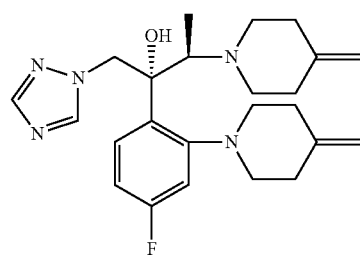 [SMILES: C=C1CCN(c2cc(F)ccc2[C@@](O)(Cn2cncn2)[C@@H](C)N2CCC(=C)CC2)CC1]

in quantities below 0.1% calculated as HPLC area % (A %) at 210 nm.

* * * * *